United States Patent [19]
Allington

[11] Patent Number: 5,685,965
[45] Date of Patent: Nov. 11, 1997

[54] CAPILLARY ELECTROPHORESIS TECHNIQUE

[75] Inventor: Robert William Allington, Lincoln, Nebr.

[73] Assignee: Isco, Inc., Lincoln, Nebr.

[21] Appl. No.: 683,680

[22] Filed: Jul. 17, 1996

Related U.S. Application Data

[62] Division of Ser. No. 561,552, Nov. 21, 1995, Pat. No. 5,626,732, which is a continuation of Ser. No. 212,241, Mar. 14, 1994, abandoned, which is a division of Ser. No. 277,566, Nov. 29, 1988, Pat. No. 5,354,440.

[51] Int. Cl.$^6$ .................. G01N 27/26; G01N 27/447
[52] U.S. Cl. .................. 204/451; 204/452; 204/453; 204/601; 204/603
[58] Field of Search .................. 204/451, 452, 204/453, 454, 455, 601, 602, 603, 604

[56] References Cited

U.S. PATENT DOCUMENTS

| | | | |
|---|---|---|---|
| 3,453,200 | 7/1969 | Allington | 204/600 |
| 3,948,753 | 4/1976 | Arlinger | 204/601 |
| 4,523,097 | 6/1985 | Allington | 250/458.1 |
| 4,726,680 | 2/1988 | Allington | 356/319 |
| 4,898,658 | 2/1990 | Karger et al. | 204/603 |
| 4,911,807 | 3/1990 | Burd | 204/453 |
| 5,045,172 | 9/1991 | Guzman | 204/452 |
| 5,085,757 | 2/1992 | Karger et al. | 204/603 |
| 5,169,511 | 12/1992 | Allington et al. | 204/451 |

FOREIGN PATENT DOCUMENTS

| | | |
|---|---|---|
| 0 329 341 | 8/1989 | European Pat. Off. . |
| 0 339 779 | 11/1989 | European Pat. Off. . |
| 0 339 781 | 11/1989 | European Pat. Off. . |
| 0 371 573 | 11/1989 | European Pat. Off. . |
| WO89/04966 | 6/1989 | WIPO . |

OTHER PUBLICATIONS

*Ullmanns Encyklopadie der technischen Chemie;* Dr. Hans Kelker; 4th edition, vol. 5, "Analysen—and MeBverfahren", 1980, Verlag Chemie GmbH, Weinheim, DE, pp. 217 and 231–233. (See English translation).

"Fraction Collector For Capillary Zone Electrophoresis" by Donald J. Rose and James W. Jorgenson; *Journal of Chromatography,* 438 (Apr. 1988) pp. 23–34.

"Characterization and Automation of Sample Introduction Methods for Capillary Zone Electrophoresis" by Donald J. Rose, Jr. and James Jorgenson *Anal. Chem.* Apr. 1988, 60, 642–648.

"Fully Automated Capillary Electrophoresis" by B. J. Wanders, et al., eleventh international symposium on capillary chromatography; May 14–17, 1990; pp. 880–884.

*Primary Examiner*—Kathryn L. Gorgos
*Assistant Examiner*—John S. Starsiak, Jr.
*Attorney, Agent, or Firm*—Vincent L. Carney

[57] ABSTRACT

To detect bands in an electrophoresis capillary tube having a liquid separating medium, a light source and a light detector of a monitor are positioned on opposite sides of the capillary tube with the light source transmitting light through a first slit and light passing to the detector through a second slit after it has passed through the capillary tube. The first and second slits are aligned with the direction of motion of bands, have a maximum length of less than 500 micrometers and a maximum width of less than 200 micrometers. There are no vertical lengths in the capillary tube having a dimension greater than one third of its length between a sample injecting end and a detecting end of the capillary tube. A sample injector includes a vacuum chamber communicating with one end of the capillary tube to pull sample into the other end and a pressure sensor to measure the pressure in said vacuum chamber and generate a signal indicative thereof and integrate it to indicate the amount of sample pulled into the system.

14 Claims, 5 Drawing Sheets

FIG. 3
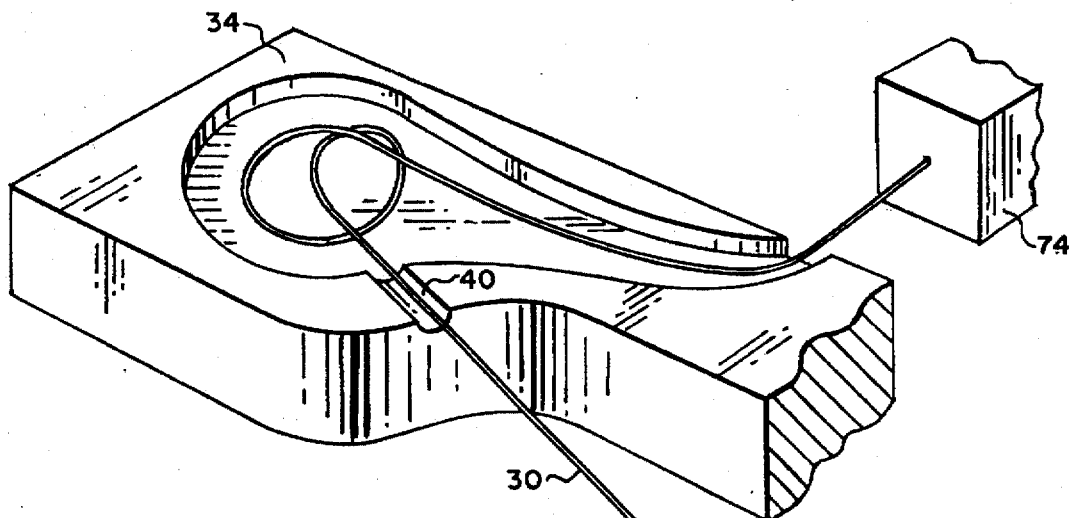
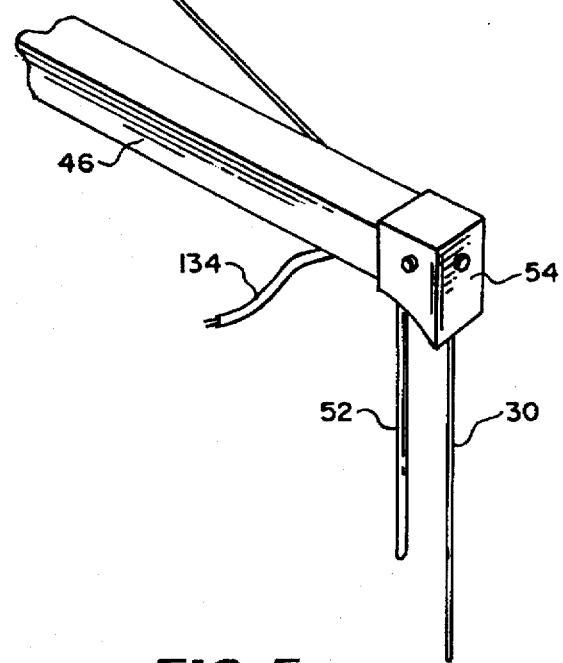
FIG. 4
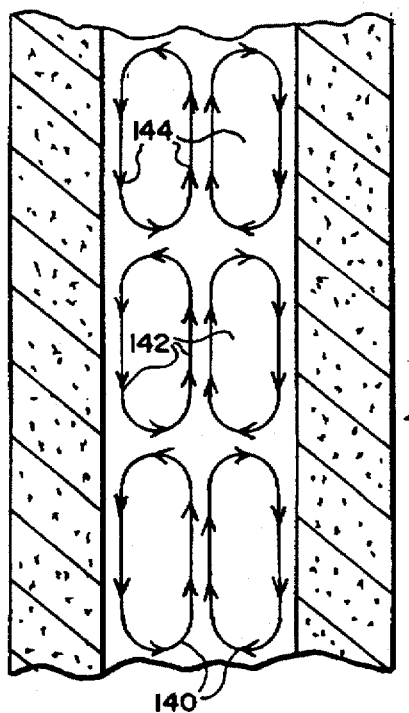
FIG. 5
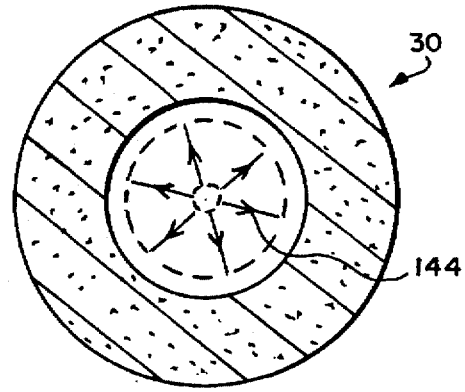

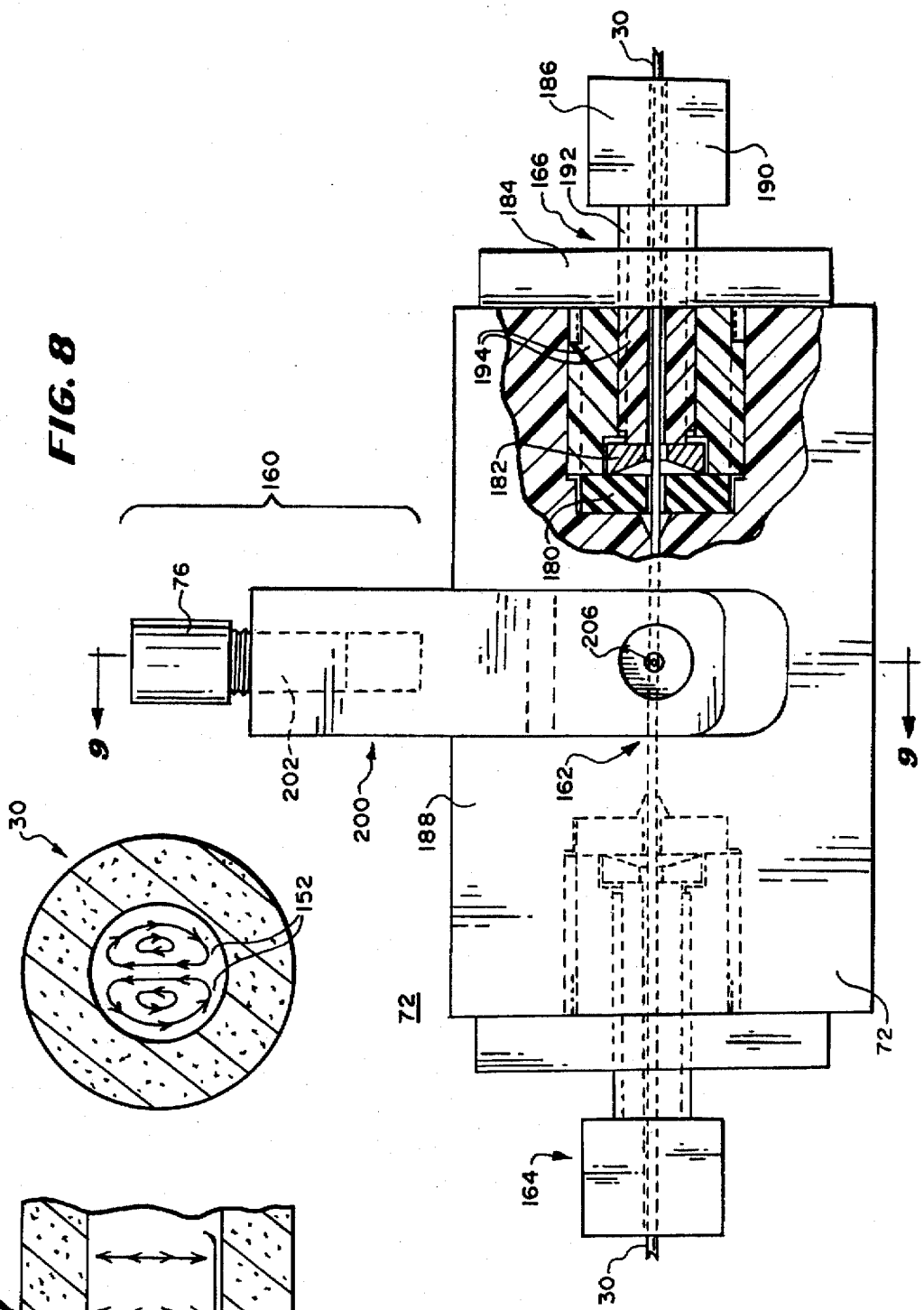

CAPILLARY ELECTROPHORESIS TECHNIQUE

RELATED CASES

This application is a division of U.S. patent application Ser. No. 08/561,552, filed Nov. 21, 1995, now U.S. Pat. No. 5,626,732 which is a file wrapper continuation of U.S. patent application Ser. No. 08/212,241, filed Mar. 14, 1994, now abandoned, which is a streamline division of U.S. patent application Ser. No. 07/277,566, filed Nov. 29, 1988, now U.S. Pat. No. 5,354,440.

BACKGROUND OF THE INVENTION

This invention relates to techniques in the separation sciences and more particularly to techniques for: (1) injecting samples into a separating apparatus; (2) separating molecular species of the samples with low band spreading; and (3) monitoring the separated molecular species of the samples.

It is known in the separation sciences to automatically inject samples into a separating apparatus, separate the different molecular species from each other and detect the bands after they have been separated. One type of such separating apparatus performs separation by electrophoresis and is known as an electrophoresis apparatus. In this process, the samples are separated in a medium as the molecular species are moved through the medium under the influence of an electrical potential.

One class of electrophoresis apparatus is a capillary electrophoresis apparatus. In a capillary electrophoresis apparatus, the medium is in a capillary tube. This tube is usually made of fused quartz. The electrophoresis medium may be a gel or liquid in capillary electrophoresis.

To sense the separated bands of molecular species, a detector transmits light through the medium phase and senses the species as they move along the medium by differences in absorbance of the light. In one class of electrophoresis apparatus, the sensing of molecular species is accomplished by transmitting light from a light source section through the medium and into a light detecting section. The light detector is positioned in the light detection section where it receives light and converts the light to an electrical signal representing the transmittance of light through a band.

In one type of prior art detector of this class, light is transmitted through one narrow slit and one larger opening in the light path between the source and the light sensor or no narrow slits so as to utilize maximum light flux.

Without the single narrow slit, some of the light flux passes through the medium to the detector, but other parts of the light flux bypass the medium. The flux passes around the medium through the walls of the quartz capillary tube and to the detector. This bypassed light results in a high level of background light which reduces the sensitivity of the detector. A conventional method of reducing background light is to use one narrow slit and collimated light. This arrangement, if applied to capillary electrophoresis, has a disadvantage in that the light level for detection is so low that there is excessive noise in relation to the strength of the electrical signals supplied by the detector. This excessive noise is quantum noise.

Another aspect of the prior art capillary electrophoresis apparatus is that, under some circumstances, a relatively high potential is used to increase the speed of migration of the molecular species through the electrophoresis medium. This is intended to increase the sharpness of the peaks and provide better resolution. The electrophoresis medium in prior capillary electrophoresis apparatus (inside diameter of capillary tube less than 0.01 inch) has a vertical orientation at least at some locations.

This prior art technique has an unobvious disadvantage. It has been discovered that vertical portions of the column reduce the resolution of the bands of molecular species being separated in a liquid electrophoresis medium in an unexpected manner. It is believed that this reduction in resolution occurs because the high electrical potential through the column raises the temperature and causes movement of the medium phase by convection. The convection currents have vertical components of motion at some locations which differ in direction or velocity from the vertical components in other locations. Some of the components of motion are axial with respect to the capillary tube, causing axial mixing and degradation of resolution.

Since the center of the medium is warmest because of its distance from cooling surfaces, the liquified medium in the central portion rises upwardly. The medium is cooled along its sides and moves downwardly as the center moves upwardly. The convection takes place in cells located adjacent to each other along the longitudinal axis of a verticle elongated separating medium. This effect is believed to take place particularly in capillary electrophoresis apparatuses.

Because the convection currents in the medium have a component of motion in the direction of migration of the molecular species in a vertical portion of the medium, the velocities of movement of the molecular species in different portions of a band are changed with respect to each other. This causes band spreading and a reduction of resolution.

The disadvantages caused by the convection currents may be minimized by using a small internal diameter capillary tube to hold the medium because: (1) more heat per unit of length is generated in a larger capillary tube; and (2) there is a longer thermal path to the inside will of a larger capillary tube than a smaller capillary tube and more space for convection cells to form. On the other hand, small capillaries result in small peak volumes making detection less sensitive.

One type of sample injector injects very small samples by applying a vacuum on the end of the separating apparatus opposite to the source of the sample to draw a small portion of the sample into the separating apparatus.

The prior art sample injectors of this type control the amount of sample by timing the period through which the vacuum is applied. The time is determined by experience. This type of prior art sample injector has a disadvantage of not being as precise as desired.

In accordance with the apparatus for detecting bands having a predeterminded direction of motion in a separation medium comprise: a light source; a light detector; and means for positioning said light source and light detector on opposite sides of said separating medium the apparatus is characterized in that the light source includes a first slit through which light passes and the detector includes a second slit for receiving light after it has passed through said medium; the first and second slits being aligned with the predetermined direction of motion of said bands the maximum width of said first and second slits is no greater than three times nor less than one-half the inner diameter of said separation medium; and the maximum length of said slit is no greater than one hundred times the diameter of said separating medium.

Advantageously, the maximum length of each of said first and second slits is less than 500 micrometers, the maximum width is less than 200 micrometers, and the first and second slits are positioned at distances no greater than 1500 micrometers from each other. There are a means for adjusting the slits with respect to each other and means for detecting light passing through said second slit. The separation medium is within a capillary tube and in which the distance between the slits is between one and three times the outside diameter of the capillary tube. The apparatus includes a capillary tube; having a diameter no greater than 700 micrometers; and being substantially horizontal for a continuous portion between an injector and detector with no vertical lengths having a dimension greater than one third of its length between the injecting means and the detecting means; said portion including said means for detecting at least up to the point on said capillary tube where the sensing takes place. There may be a sample injector having a vacuum source; a source of samples; and a vacuum chamber. The vacuum chamber communicates with one end of a separating means; said separating means having a second end which communicates with a sample source, means for causing a vacuum in said vacuum chamber to draw sample from said source of sample wherein sample is pulled at a slow rate into said second end of the separating means; and pressure measuring means adapted to measure the pressure in said vacuum chamber and generate a signal indicative thereof.

The pressure sensor is adapted to control the transfer of sample and the pressure measuring device includes an integrator for integrating a signal representing the pressure in the vacuum chamber wherein the amount of the sample introduced into said second end of the separation means may be detected. There is a means for adjusting the location of said slits in a direction at an angle to the longitudinal axis of said separation medium wherein there is high transmission of light when said slits are substantially aligned with the longitudinal axis of said separating medium, lower transmission as said slits move in either direction toward the edge of said separating medium and good transmission outside of said separating medium. The first section includes a light source and an outlet slit through which light is emitted. The second section includes a light sensor and an inlet slit corresponding substantially in size to the outlet slit of the first section.

The first and second sections are mounted on opposite sides of a separating medium in an apparatus for separating molecular species, with their slits aligned with each other. With this arrangement, the light sensor receives light passing through both slits and through the medium containing molecular species to be sensed. The electrical signal resulting from the detector is utilized to detect peaks in the column.

In the preferred embodiment, the column is a capillary electrophoresis column having a bore less than 150 micrometers in diameter. The first and second slits are positioned from each other on opposite sides of the capillary tube and less than 1500 micrometers from each other. Their lengths are not substantially larger than the width of the bands being detected. The widths of the slits are less than the outer diameters of the capillary tubes and preferably less than: (1) one half of the outer diameter of the capillary tubes; and (2) three times the inside diameter of the capillary tubes.

The slits are aligned with the center of the separation medium by applying light through the light source section into the light detection section. As the slits are moved orthogonally to the longitudinal axis of a capillary tube filled with a transparent medium of refractive index greater than 1, a sharp increase in output electricity indicates alignment of the two slits with a desirable portion of the capillary tube such as with the longitudinal axis. This indication of alignment is particularly effective in capillary electrophoresis because the light drops off at each side of the capillary tube and reaches a peak at the center.

To decrease band spreading during electrophoresis, a length of the capillary is positioned substantially horizontally. High voltage electrophoresis is used while the molecular species are in the horizontal portion. Lower voltages are used while the molecular species are in a portion having a substantial vertical component. With the capillary tube substantially horizontal, convective movement in the direction of migration of the molecular species is reduced, even when relatively high voltages are used. This reduces band spreading.

To inject samples into a separating apparatus, a sample injector includes a sample inlet orifice and a vacuum orifice positioned in a vacuum chamber so that the sample is drawn by vacuum into position within the separating apparatus upon the opening of a valve. A pressure monitor is mounted to the vaccum chamber to develop a signal indicating the pressure and its fluctuations, if any, as the sample enters the sample chamber for separating in the separation apparatus. In the preferred embodiment the sample chamber is the inlet to the capillary.

By measuring the negative pressure in the vacuum chamber with respect to time, the amount of sample which has been introduced can be determined very repeatably. This measurement may control the introduction of .sample such as for example by controlling the vacuum valve in the preferred embodiment or by controlling a sample valve in other embodiments.

In the preferred embodiment, the vacuum pressure is measured and the signal representing the vaccum pressure is integrated. This time integral is accurately proportional to the amount of sample pulled into the capillary, because the flow rate within the capillary is accurately proportional to the vaccum pressure. In some embodiments, a valve controlling the flow of sample and/or the application of vacuum is controlled to permit the flow of sample for a preset time and the integrated signal recorded. In other embodiments, this recorded signal is compared to the desired signal and the time of sample flow adjusted after each measured injection until the precise time for the desired value of sample is determined.

In the latter technique, the valve may be opened to create vacuum pressure and maintained open continuously until a preset time is reached, at which time the valve or valves are closed. In an alternative, the valve or valves may be opened and closed several times to supply sample in increments until the proper amount of sample has been introduced. Moreover, the amount of time may be determined in a series of steps in which the amount of sample is determined between opening and closing and the opening and closing times accordingly adjusted until the proper time for introducing sample is known or recorded for use in successive runs.

To determine the proper time for introducing sample, the measurement of sample across a particular increment is determined from the integral of pressure within the vacuum chamber. If in a given period of time, the amount of sample is too great, at the next injection, the time is shortened and if the amount of sample is too low, the time is increased.

From the above description, it can be understood that the separating apparatus of this invention has several advantages, such as for example: (1) noise is reduced by the superior transmission of light from a light source through a very small sensing area into the light detector; (2) band spreading is reduced by constraining convection currents in the medium to motion in a direction orthogonal to the direction of migration of the molecular species being sensed; and (3) greater precision of sample injection is provided.

SUMMARY OF THE DRAWINGS

The above noted and other features of the invention will be better understood from the following detailed description when considered with reference to the accompanying drawings, in which:

FIG. 3 is simplified fragmentary perspective view of a portion of the apparatus of FIG. 2;

FIG. 4 is a longitudinal sectional view of a capillary tube illustrating a concept related to the invention;

FIG. 5 is a cross sectional view of the capillary tube of FIG. 4;

FIG. 6 is a longitudinal cross section of a capillary tube illustrating an aspect of the invention;

FIG. 7 is a cross sectional view of the capillary tube of FIG. 6;

FIG. 8 is a side elevational view, partly broken away and sectioned, of a flow cell useful in an embodiment of the invention;

DETAILED DESCRIPTION

Figure 1:
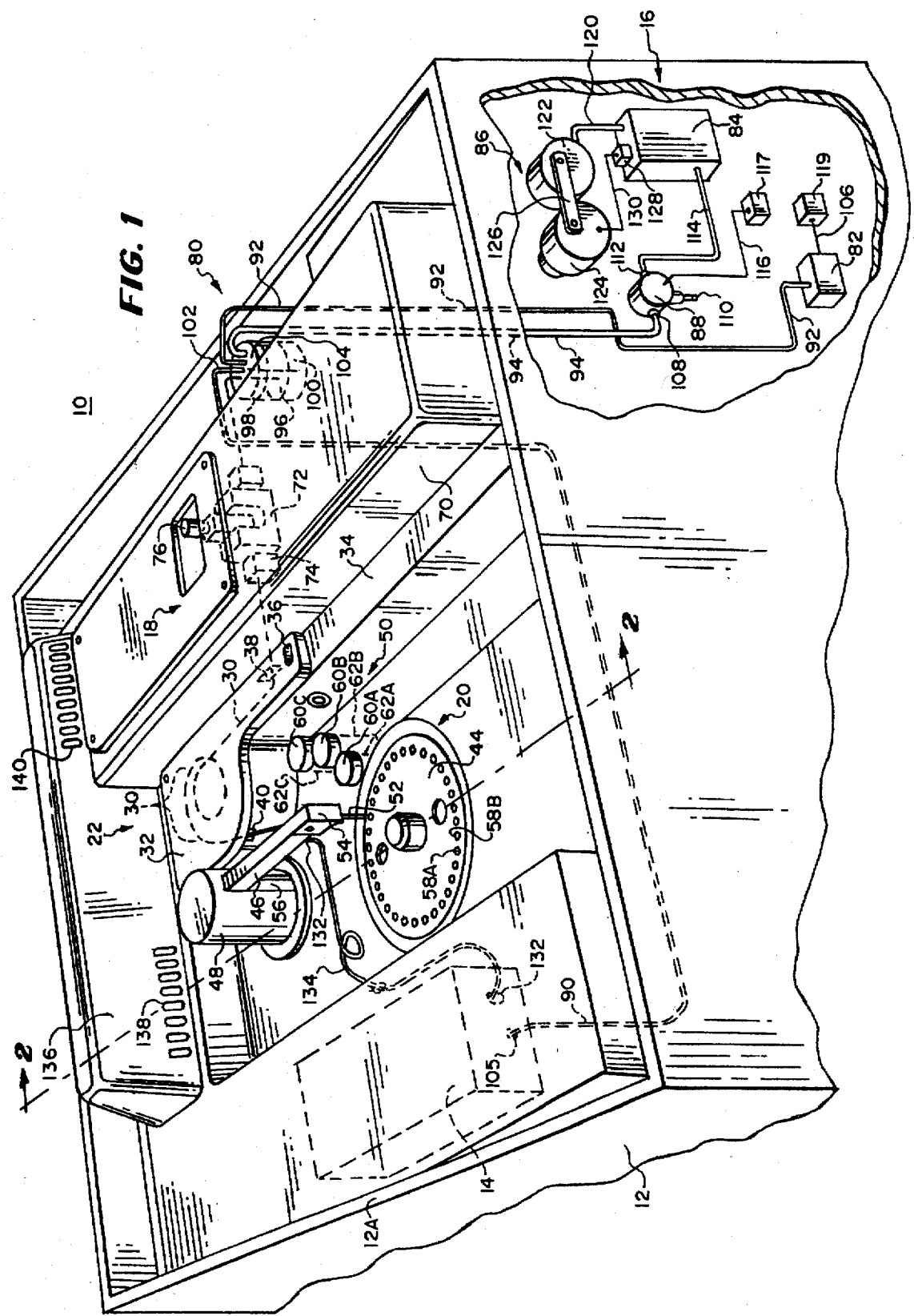
FIG. 1 is a fragmentary perspective view of an electrophoresis apparatus according to the invention and including a sample changing mechanism.

In FIG. 1, there is shown a capillary electrophoresis apparatus 10 having a cabinet 12, a power supply 14, a sample injection system 16, a sensing section 18, a sample changing system 20, and an electrophoresis section 22. The cabinet 12 is shown in FIG. 1 with its top removed. It supports the power supply 14, the sample changing system 20, the electrophoresis section 22, the sensing section 18 and the sample injection system 16, which are connected together to separate molecular species.

The electrophoresis section 22 is connected to the sample changing system 20 and adapted for maintaining at least one portion of the electrophoretic separating region of the capillary tube horizontal. The sensing section 18 is connected to the electrophoresis section 22 and includes a novel light absorbance detection cell for monitoring the separation, and an improved way of introducing a precise sample volume to be described hereinafter.

With this arrangement, the sample changer section 20 causes one end of the capillary tube 30 to contact a sample and the sample injection system 16 pulls sample into the end, and causes one end of the capillary tube to be in contact to a buffer at a potential suitable for electrophoresis. Power is applied at a high potential while the sample is within the part of the capillary tube which is horizonatal to rapidly electrophoresis with low diffusion. The separated bands are sensed by transmitting light through narrow slits on opposite sides of the separating medium in the sensor and determining the absorbance of the bands.

In this specification, "substantially horizontal", as applied to the electrophoresis medium, means horizontal enough so as to not have convection currents with a substantial component of motion in the direction of migration of the molecular species and thus sufficiently horizontal to avoid band spreading from thermal convection currents at high voltages of electrophoresis. Generally the angle of the separating medium will be less than 15 degrees from a plane orthogonal to the force of gravity. A section of horizontal capillary tube of at least 100 millimeters in length is normally used to perform such high potential electrophoresis according to one embodiment of the invention.

In the preferred embodiment, the sample changing section 20 inserts one end of the capillary tube into a sample, and after the sample injection system section 16 has pulled sample into the end, the sample changing system 20 inserts the end of the capillary tube into a buffer. Power is applied and, when the sample is in a horizontal portion of the capillary tube, the voltage is increased to speed the separation. In some embodiments the capillary tube is horizontal throughout its length of electrophoresis and the sample changer need not move the end of the capillary tube from the sample to the buffer. In this embodiment, the horizontal capillary containing sample is inserted horizontally into the buffer by means of some suitable method such as piercing a resealable container. In another embodiment, the sample containers and buffer are moved into contact with the end of the capillary tube rather than moving the end of the capillary tube.

The electrophoresis section 22 is located within the cabinet 12 for temperature control during electrophoresis and includes a capillary tube 30, a removable horizontal cover plate 32 and a horizontal ledge 34, which cover plate 32 rests on the horizontal ledge 34 in the cabinet 12. The removable horizontal cover plate 32 and horizonal ledge 34 contain the capillary tube 30 between them within a recess in the horizontal ledge 34 shaped to permit a change in the length of the capillary tube 30 between the removable horizontal cover plate 32 and horizontal ledge 34. This permits the movement of the end of the capillary tube 30 by a sample changer while the capillary tube 30 is maintained in a horizontal position even though the distance between the sample changer and the light sensor changes.

The capillary tube 30 has: (1) a first end that extends from the electrophoresis section into the sample changing system 20 where it is held for contact with the sample and buffer, which may be by movement into the sample and buffer solution; (2) a central section within the electrophoresis section which is horizontal and through which electrophoresis takes place under some circumstances at high voltage; and (3) a second end section that extends from the electrophoresis section into the sensing section 18 and sample injection system 16.

The capillary tube 30 is made of quartz in the preferred embodiment with an inside diameter of between 0.03 and 0.2 millimeter and may include any mobile separating medium. The capillary tube wall in the preferred embodiment is in the thickness range of between 0.1 and 0.2 millimeters. While a capillary tube of the conventional type for electrophoresis is contemplated for the preferred embodiment, other sizes of tubes and tubes of other materials may obviously be used.

To provide temperature control by cooling the horizontal section of capillary tube 30 within the elongated horizontal recess in ledge 34, the horizontal ledge 34 and removable horizontal cover plate 32 are preferably made of highly thermally conductive material and/or the removable horizontal cover plate 32 includes extensive perforations to facilitate cooling of the capillary tube 30. The removable horizontal cover plate 32 may be removed with handle 36.

To permit the capillary tube 30 to extend beyond the elongated recess between the removable horizontal cover plate 32 and the horizontal ledge 34 to the sample changing system 20 and the sensing section 18: (1) a notch 40 is provided at one side (the left end as viewed in FIG. 1) in horizontal ledge 34 to receive the capillary tube 30 from the sample changing system 20; and (2) another notch is provided in the other end, which is the right end as viewed in FIG. 1, to permit the capillary tube 30 to pass out of the electrophoresis section through hole 38 in the sensing section 18.

To supply samples to the capillary tube 30, the sample changing system 20 includes a sample holding reel 44, a movable arm 46, a rotor head 48 and an electrolyte section 50. The sample holding reel 44 and electrolyte section 50 contain sample and electrolyte in spaced apart containers and the movable arm 46 is carried by the rotor head 48 and is movable in two directions to insert an electrode in the electrolyte and the end of the capillary tube 30 into the electrolyte and sample.

This electrode 52 and the capillary tube 30 are mounted by a bracket 54 to moveable arm 46 of the sample changing system 20. The bracket 54 mounts the capillary tube 30 at a horizontal level that is, when the end capillary tube is lowered into contact with the electrolyte, the same as the level of the recess in the horizontal cover plate 34 and the level of the sensor 72 so as to maximize the length that is horizontal. In one embodiment, the arm moves up and down through slot 56 in rotor head 48 of the sample changing system 20. In another embodiment, the arm and its shaft move up and down and rotate and the rotor casing is not necessary, This enables dipping the capillary tube 30 in sample vials indicated as 58A, 58B, (etc.) in the removable sample holding reel 44. The removable sample holding reel 44 is programmably rotatable to bring any of its 40 sample tubes under capillary tube 30 and rotor head 48 is rotatable to place the capillary tube 30 either over a sample tube or over electrolyte vessels 60A, 60B or 60C in the electrolyte section 50.

When the desired electrolyte vessel or a sample tube is selected by rotation of rotor head 48, movable arm 46 moves downward to put the end of capillary tube 30 either in contact with the sample in the sample tube or with the electrolyte 62A, 62B or 62C in an electrolyte vessel. When the end of the capillary tube 30 dips into the electrolyte in an electrolyte vessel, platinum electrode 52 also dips into the vessel. Thus, the desired electrolyte vessel is selected both by the electrode 52 and the capillary tube 30.

Several alternate embodiments are possible for bringing the sample into contact with the end of the capillary tube 30 and for establishing a potential across the tube for electrophoresis. For example, there may be a motionless but easily removable electrode "manifold" that dips multiple platinum electrodes simultaneously into all of the electrolyte vessels rather than dipping both the electrode and the capillary into the electrolyte vessels as described above to establish a potential across the tube. This action establishes one potential on the capillary tube 30 for electrophoresis with the other electrical connection to be described hereinafter as a permanent connection in a buffer although the circuit may be broken and established at programmed times.

The sensing section 18 (FIG. 1) includes an absorbance monitor 70 and a sensor 72. The absorbance monitor 70 and sensor 72 utilize the optics, circuitry and structure of the absorbance detector described in U.S. Pat. Nos. 4,726,680 and 4,523,097 for liquid chromatography absorbance detectors. The absorbance monitor 70 incorporates a light source for illuminating one side of sensor 72 and a light detector for detecting light exiting the opposite side of sensor 72. It is substantially the same detector turned on its side so that the flow cell is on top and has a horizontal flow axis or plane, instead of being mounted on the side of the detector and having a vertical flow axis or plane. Of course, the flow cell and separating system are adapted for capillary electrophoresis as described herein, instead of for liquid chromatography as described in the foregoing patents.

To sense bands, the capillary tube 30 enters sensor 72 (FIG. 1) through a tubing-holding fitting 74 (FIG. 1). Sensor 72 is equipped with adjustable slits to align a very narrow measuring light beam so that it goes exactly through the liquid filled part of the capillary tube 30. The position of the slits is adjusted by screw adjustment 76 (FIG. 1) as described hereinafter.

The sample injection system 16 includes a controllable pressure buffer and electrode assembly 80, an electrical interface 82, a low vacuum tank 84 and a pressure control solenoid valve 88. The buffer and electrode assembly 80 measures the vacuum pressure in contact with the surface of the buffer during sample injection and provides an electrical connection to the capillary tube 30 during electrophoresis. For these purposes, it is electrically connected to the power supply 14 through a conductor 90, to the electrical interface 82 to provide a measured pressure signal through a cable 92 and to the pressure control solenoid valve 88 through a pressure line or connecting tubing 94. The pressure control solenoid valve 88 communicates with the vacuum tank 84 which is connected to the pump assembly 86. The electrical interface 82 may include an integrator to provide a signal proportional to the sample or integration and may be performed in a computer connected to the electrical interface 82.

The capillary tube 30 extends into electrode buffer vessel 96 fitted with removable cap 98 as it exits the sensor 72. The capillary tube no longer needs to be kept horizontal after leaving the sensor 72 since the separation has already been measured optically. The vessel is partly filled with electrolyte buffer 100.

To establish an electrical connection through the capillary tube 30 for electrophoresis, the removable cap 98 is pierced by platinum electrode 102 and the capillary tube 30 and platinum electrode 102 dip into electrolyte buffer 100. Above the removable cap 98, electrical conductor 90 is connected to electrode 102 and to the ground terminal 105 of power supply 14. Connecting tubing 94 also pierces cap 98, but does not dip into electrolyte buffer 100.

To draw a controlled amount of sample into the end of the capillary tube 30 with a measured pressure; (1) connecting tubing 94, electrode 102 and capillary tube 30 are sealed airtight into the removable cap 98; (2) the removable cap 98 is sealed airtightly to electrode buffer vessel 96; and (3) a pressure sensor 104, mounted on the top of removable cap 98, communicates directly to the interior of the electrode buffer vessel 96 and senses the pressure therein. The electrical connection 92 connects the pressure sensor 104 to an electrical interface 82 which is connected by a lead 106 to a conventional controller or computer 119 not described in connection with FIG. 1. In the alternative, the signals may be recorded with conventional recording equipment and the operation of the sample injector and movable arm 46 may be manually performed.

To supply negative pressure to the buffer and sample measuring assembly 80, the connecting tubing 94 communicates with the common port 108 of pressure control solenoid valve 88. Normally open port 110 of this valve is vented to the atmosphere and the normally closed connection 112 of this valve is connected to tubing 114 which leads to low-vacuum tank 84 so that energization of the pressure control solenoid valve 88 applies vacuum pressure to the buffer and sample measuring assembly 80.

To energize the pressure control solenoid valve 88, a conductor 116 is electrically connected to a controller or computer or a manually-operated electrical switch 117 connected to a source of power and supplies power to the solenoid of the pressure control solenoid valve 88. This controller or manually-operated electrical switch supplies signals to initiate the sample injection while the capillary is held in the sample well by the movable arm 46.

To maintain the vacuum pressure in the low-pressure vacuum tank 84, tubing 120 connects the low-pressure vacuum tank 84 to vacuum pump assembly 86. The vacuum pump assembly 86 includes a vacuum pump 122 mechanically connected to electric motor 124 through coupling 126. A vacuum sensor 128 turns on motor 124 through a signal on lead 130 when the pressure in the tank becomes too high. This establishes a controlled negative pressure in the tank 84. Preferably, the setting of the vacuum sensor is adjustable or programmable.

The high voltage power supply 14 is located inside the cabinet 12 and is fitted with ground terminal 105 and high voltage terminal 132. The power supply 14 is preferably capable of supplying a regulated voltage from 1,000 to 40,000 volts at a current of up to 100 microamperes. A high voltage insulated cable 134 is connected to high voltage terminal 132 and terminates in platinum wire electrode 52.

A conventional air cooling and temperature control unit (not shown) are housed in cabinet 12. A fan incorporated in this unit blows temperature conditioned air out through vent slots 140 located in venting unit 136. Return air to the air conditioning mechanism is through vent slots 138. This air conditioning feature ensures that the electrophoresis process operates at a repeatable temperature that does not vary significantly over a period of time. The air enters and flows above the sensor 72, and then is routed past the capillary tube between its sample inlet end and the sensor 72 by conventional baffling not shown in the figure. Temperature control of electrophoretic separations is a common feature of electrophoresis apparatus.

Figure 2:
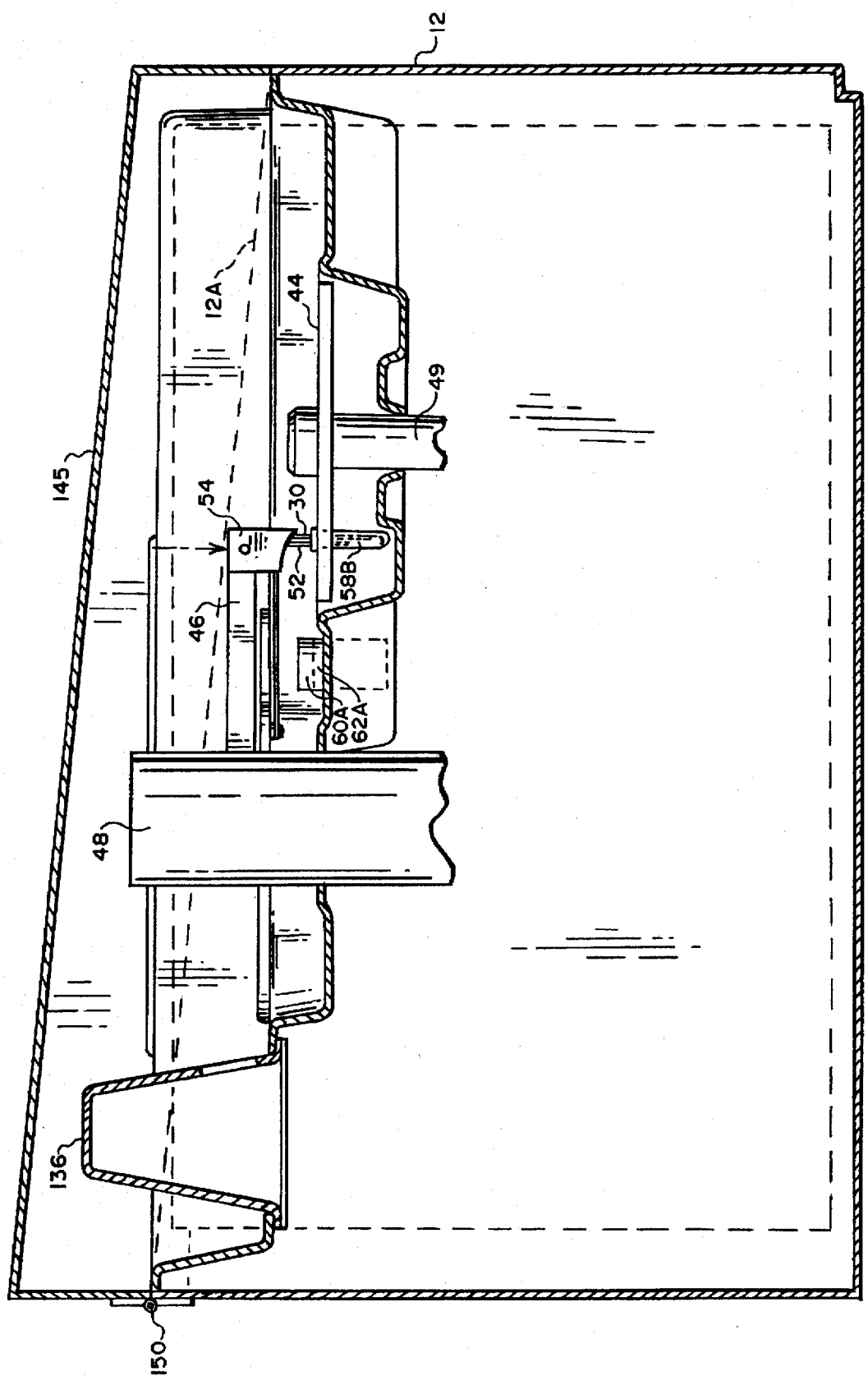
FIG. 2 is an irregular cross sectional view taken generally through the sample changing mechanism of the apparatus shown in FIG. 1, looking from the left.

In FIG. 2, there is shown a sectional view of the cabinet 12 taken through lines 2—2 of FIG. 1 and showing the rotor head 48, movable arm 46, capillary tube 30, sample vials such as 58B and a lid 144. As shown in this view, the cabinet 12 is: (1) insulated; (2) includes a top surface 12A that slopes upward from front to back; and (3) is fitted with a lid 144 (FIG. 2) which preferentially has metal sides and a transparent top. The lid 144 is hinged to the cabinet 12 with hinge or hinges 150. The cabinet 12 preferentially has an outer metal surface which, along with the sides of the lid 144, are electrically grounded for safety. As shown in this view, the bracket 54 mounts the capillary tube 30 at a location adjacent to the electrode 52 so that the capillary tube 30 is insertable into the sample vial 58B and the electrode 52 may be moved to the buffer compartment 62A for insertion in the buffer 60A by rotating the arm 46.

When a new sample is desired, a rotor 49 rotates the table 44 to move a new sample in position under the arm and the arm is swingable between the buffer compartment 62A and the sample housing reel 44. As it rotates, the capillary tube 30 extends through the notch 40 in the removable horizontal ledge 32 (FIG. 1) where it is inserted into coils therein which expand or contract to take more or less tubing. With this arrangement, the capillary tube 30 remains horizontal between its connection with the bracket 54, the recess in the removable horizontal ledge 32 (FIG. 1) and the sensor 72 (FIG. 1).

In FIG. 3, there is shown a simplified fragmentary view of a movable arm 46, an electrical conductor 134 for high voltage, a capillary tube 30, and a sensor 72 with the capillary tube 30 being positioned in a recess in the ledge 34 (the cover plate 32 is removed in this view). The bracket 54 is shown having a first opening adapted to mount one end of the capillary tube 30 and a second opening adapted to connect the electrode 52 to the conductor 134 for movement with the end of the capillary tube 30. As best shown in this view, the horizontal ledge 34 includes a recess in which the capillary tube 30 is coiled so that it may receive more or less tubing as the movable arm 46 swings between a buffer location and a sample location. The bracket 54 supporting the capillary tube 30, the recess in the surface 34 and the fitting for the sensor 72 are all in the same horizontal plane so that, as the electrophoresis apparatus is operated, the capillary remains horizontal.

In FIG. 4, there is shown an axial section, and in FIG. 5, there is shown an orthogonal cross section of a capillary electrophoresis tube 30 that is not horizontal. As shown in this view, there are convection patterns in a liquid electrophoresis medium within the capillary electrophoresis tube when high voltage has caused heating of the liquid. It is a tube whose axis is either vertical or partly vertical. The capillary tube 30 is shown magnified in this view but with exaggeratedly thin walls.

Typically the inside diameter of the tube is 50 to 75 micrometers and the outside diameter is 375 micrometers. The length of the interior of the tube is filled with a liquid buffer electrolyte. An electric field is established along the axis of the tube by conventional means and electric current flows through the tube. The electric current, although small, is sufficient to cause heating of the electrolyte.

The heat dissipation is initially constant throughout the cross section of the electrolyte, and heat is dissipated from the electrolyte, through the walls of the quartz capillary tube and to the surrounding air. Since the electrolyte is cooled along the inner tube walls, its temperature is higher in the center of the tube than at the inside diameter of the tube. This effect is regenerative, as the higher temperature at the center increases the conductivity there, causing more current to flow (and more heat to be generated) in the center.

If the tube is disposed with its axis at least partly vertical, there is a tendency for convection cells indicated at 140, 142 and 144 to form within the capillary tube 30. This is because the electrolyte is warmer and therefore less dense in the center of the tube and cooler and therefore more dense at the edge of the tube. These convection cells have a component of fluid motion that is parallel to the axis of the tube and therefore tend to spread narrow zones of partially separated electrophoresed sample in the axial direction. This is undesirable as it decreases the resolution of the separation.

One method of avoiding this band spreading is to keep the electric power dissipation within the tube low enough so that these convection cells do not form. This sets an undesirable limitation on the maximum amount of electric field that can be used and therefore sets a limitation on the speed of the separation.

A faster separation may be obtained in accordance with the novel technique described in this application using a higher electric field. This faster separation is desirable for more efficient use of time and to decrease peak broadening due to time-dependent phenomena such as diffusion. Alternatively, a larger inside diameter horizontal capillary tube can be used instead of or in addition to a higher field. The larger diameter has a significant advantage because larger cross-sectional area separated peaks result. These larger volume peaks can be detected with greater concentration sensitivity than smaller volume peaks.

In FIG. 6 there is shown an axial section, and in FIG. 7, there is shown an orthogonal cross section of a the capillary tube 30 illustrating the convection patterns that result in a horizontal capillary tube operated at sufficiently high voltage and current for convection to take place.

When the tube is horizontal, convection is perpendicular to the tube axis as shown by the convection patterns at 152. Mixing within the tube augmented by convection in this direction does not degrade the integrity of separated or partially separated sample peaks because the sample zone concentration is constant in any plane perpendicular to the axis of the tube. Although the convection cell for a horizontal tube also exhibits rising flow in the center where the liquid is warmer and falling flow at the interior walls of the tube where the liquid is cooler, the resulting motion is perpendicular to the tube axis instead of parallel to the tube axis as in the case of a vertically oriented capillary tube. Therefore such convection does not degrade the resolution of the separation.

In FIG. 8, there is shown a side view partly broken out and sectioned showing the sensor 72 having an adjustment section 160, an optical slit section 162, a first fitting assembly 164 for the capillary tube 30, and a second fitting assembly 166 for the capillary tube 30. The capillary tube 30 is received in the first and second fittings 164 and 166, which cause the capillary tube 30 to extend along the axis of the sensor 72 and between the slits in the optical slit section 162. The location of the two slits in a direction perpendicular to the axis of the capillary tube 30 is adjusted by the adjustment section 160.

The sensor 72 is attached to a cassette or mounting plate for mounting in the absorbance monitor 70 (FIG. 1) and receives the capillary tube 30. To mount the capillary tube 30, the two fitting assemblies 164 and 166 are adjustable. They are identical in structure and only the fitting assembly 166 will be described in detail herein.

The fitting assembly 166 includes a rubber washer 180, a stainless steel squeezer 182, a plastic threaded closure 184 and a plastic threaded fastener 186. The threaded fastener 186 is positioned to be tightened to hold the threaded closure 184 in place where it supports a threaded sleeve. The threaded fastener 186 also presses the stainless squeezer 182 against the rubber washer 180 so as to provide a seal around the capillary tube 30.

In the preferred embodiment, the housing 188 of the sensor 72, the threaded fastener 186 and the threaded closure 184 are all formed of a relatively hard plastic such as Delrin (trademark of the DuPont Corporation). The washer 180 is a flexible, elastomeric material which may be the thermoplastic rubber Kraton. A central aperture extends through the washer 180, the stainless steel squeezer 182, the threaded closure 184 and the fastener 186 to accommodate the capillary tube 30 which extends along the longitudinal axis, past the optical slit section 162 where the optical sensing is performed and through the fitting assembly 164 on the opposite side of the sensor 72.

To force the washer 180 around the capillary tube 30, the washer 180 is generally cylindrical with a cylindrical central opening receiving the capillary tube 30. It fits conformably in a counterbore within the housing 188 of the sensor. The stainless steel squeezer 182 is generally cylindrical but has an inwardly tapering cone positioned adjacent to the washer 180 and a central aperture to accommodate the capillary tube 30 so that when it is pressed inwardly, it forces the washer inwardly towards its central opening and outwardly against the counterbore.

To force the stainless steel squeezer 182 against the washer 180, the threaded fastener 186 includes a thumb handle 190 and a threaded shank 192, with the threaded shank 192 extending downwardly through the plastic threaded closure 184 where it engages a correspondingly threaded metal sleeve 194 threaded into a tapped hole of the Delrin housing. The threads within the tapped hole are within a metal sleeve molded within the aperture of the Delrin housing so as to remain fixed in position and still accommodate threads. The mechanism of the fittings are designed to accommodate the capillary tube 30 in such a way that the capillary tube 30 is held immobile in the light sensor 72.

Figure 9:
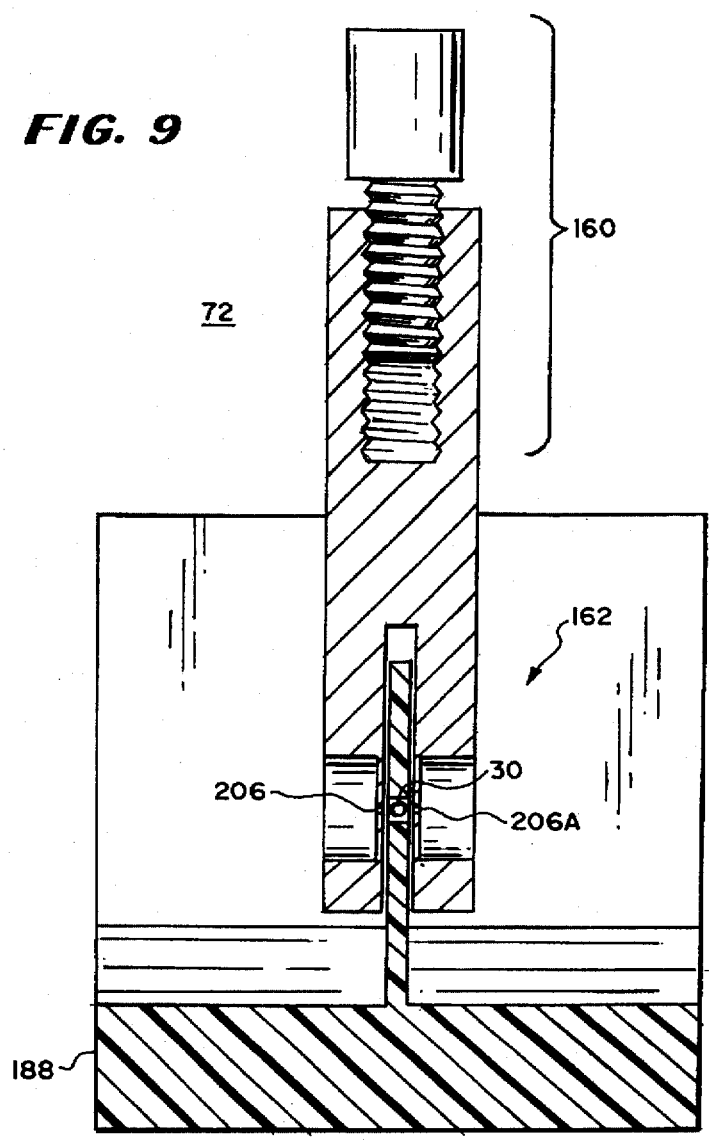
FIG. 9 is a sectional view taken through lines 9—9 of FIG. 8.

The adjustment section 160 includes an adjustment screw 76 fixedly mounted (by convential means not shown in the figure) with respect to the housing 188 and an optical slit carriage 200. The optical slit carriage 200 is stainless steel and threaded at 202 in its upper portion with internal threads complementary to the external threads on a shank of the tightening screw 76 so that as the adjustment screw 76 is rotated, the carriage is moved up and down with respect to the housing 188 of the sensor 72. The optical slit section 162 is mounted to the bottom of the optical slit carriage 200 so as to be raised and lowered therewith and includes on each side a relatively short optical slit 206 having a longitudinal axis aligned with the longitudinal axis of the capillary tube 30. There are two such slits which closely straddle the capillary tube 30 (FIG. 9) a cross section through line 9—9 of FIG. 8, more clearly shown the relationship of the two slits 206 and 206A to the capillary tube 30. FIG. 9 shows the narrow dimension of the slits, which is 100 micrometers in the preferred embodiment. Preferably, the distance between the slits is between one and three times the outside diameter of the capillary tube.

More specifically, the rubber washer 180 is compressed around the capillary tube 30 to hold the tube in place. The rubber washer 180 preferably is made of white, food grade, Kraton (trademark) thermoplastic rubber which does not deposit any ultraviolet light absorbing materials on the quartz tube as the tube is pushed through the washer. Kraton is available from Shell Corporation. The rubber is compressed radially to tighten around the tube by pushing the female cone-shaped stainless steel squeezer 182 against it by turning a plastic threaded fastener 186. The threaded fastener 186, stainless steel squeezer 182 and washer 180 are captivated within the housing 188 of the light sensor 72 by the threaded closure 184 which screws into a threaded recess in the housing 188. The tightener, captivator and housing are advantageously made out of Delrin (trademark of DuPont) plastic.

The optical slit carriage 200 is moved with the adjustment screw 76 to center a pair of optical slits, one of which is shown at 206, each being 0.01 inch (250 micrometers) long by 0.004 inch (100 micrometers) wide, over the capillary tube 30 extending through the light sensor. The dual slits are exactly corresponding elements mounted exactly opposite each other across a bifurcation of the optical slit carriage (FIG. 9). The capillary tube 30 lies within the bifurcation. The long direction of the slit is parallel to the axis of the capillary tube 30. When the adjustment screw 76 is turned, the optical slit 206 moves transversely with respect to the capillary tube 30. The capillary tube 30 is firmly held within the bifurcation by two holders.

To use the light sensor, first the protective polyimide protective coating of the quartz capillary tube 30 must be removed because it absorbs ultraviolet light. This is easily done by burning it off with a match or cigarette lighter in the region which is to be located between the optical slits. After burning the coating off, the capillary tubing 30 must be cleaned with very pure acetone. Any area of the capillary tubing 30 that does not have an intact polyamide coating is very fragile and must be handled with more than normal care.

Both Delrin tighteners on the light sensor 72 are loosened, and the capillary tube 30 is gently fed through one tightener, through the rubber washer, through the optical slit region, through the other washer and tightener, and moved to the desired position with the polyamide-free region of the capillary tubing 30 between the slits. Then the two tighteners are screwed down finger tight, thus firmly captivating the capillary tubing 30 in the light sensor.

Figure 10:
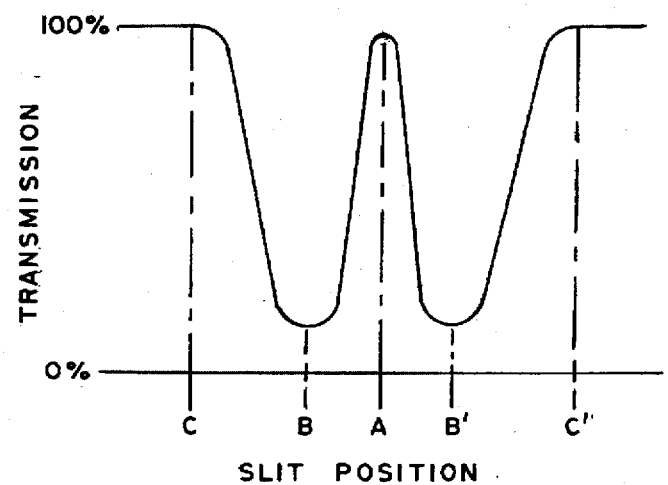
FIG. 10 is a graph containing a curve representing transmission with different positions of slits related to the embodiments of FIGS. 8 and 9.

The sensor 72 is inserted in the absorbance monitor 70 located within the cabinet 12 in FIG. 1. In FIG. 1, the sensor is generally shown at 72. The capillary tube 30 is filled with water or buffer. Light from the light source of the absorbance monitor enters one of the pair of slits in the sensor 72, and when the sensor 72 is properly adjusted, light exits the other slit and impinges upon the light detector of the absorbance monitor. To make this adjustment, the adjustment screw (shown as 76 in FIGS. 1, 8 and 9), is rotated and the indication of the absorbance monitor 70 is monitored. Starting at one extreme of rotation on the tightening screw 76, and referring to FIG. 10, the following is observed.

At slit position C, the slit is entirely beyond the capillary tube 30 and light travels through the free space between the pair of slits. As the adjustment screw 76 is rotated, the light beam cuts through the curved edge of the capillary tube 30 which deflects most of the light going through the first slit so it does not go through the second slit.

At slit position B, almost all of the light is lost, and a minimum of light transmission is indicated on the absorbance monitor.

Assuming that the capillary tube 30 is properly filled with water or electrolyte buffer (no air in the tube at the light path), continued rotation of the adjustment screw so that the pair of slits are centered on the tube greatly increases the transmission again, to a well defined maximum at proper alignment. This is shown as slit position A in FIG. 10.

Further rotation of the adjustment screw 76 produces transmission indications as shown when moving from A to B' and then from B' to C' because of symmetry in the transverse direction. The absorbance monitor should be operated with the adjustment screw 76 set to slit position A, as determined from the local maximum transmission reading of the absorbance monitor itself.

It has been found that two slits, one on each side of the capillary tube 30, instead of a single slit as in the prior art, provide lower optical noise, less baseline drift and a greater effective optical path length for the same inside diameter of the capillary tube 30 because of reduced stray light. Stray light is low with double slits even when the slit width is greater than the inside diameter of the capillary tubing such as for example a 100 micrometer slit width and 75 or 50 micrometer tubing inside diameter.

In contrast to this observation, it would be expected that two such very small slits, one on each side of the cylindrical lens formed by the capillary tube 30, would not let enough light through to be practical. Light energy severely cut by the first slit would again be cut by the second slit, leaving almost no light remaining. This expectation turns out to be wrong, in spite of the fact that the flow cell entrance slit is conventionally located at the exit focus of the monochromator of the absorbance monitor. The light is already diverging immediately upon leaving the sensor 72 entrance slit. Most of the light is also present as skew rays. Yet sufficient light goes through the second slit so that quantum (photon) noise is not a problem when using a conventional absorbance monitor.

Before operating the capillary electrophoresis apparatus, the capillary tube 30 should be arranged as shown in FIG. 1. Samples to be separated should be placed in sample tubes on sample holding reel 44. Electrolyte buffers suitable for the separation placed in electrolyte vessels 60A, 60B, 60C and 96.

The apparatus is preferably operated under the control of a conventional programmed controller or computer but may be operated by hand. In operation, if the proper buffer electrolyte is not already in the capillary tube 30, the movable arm 46 puts the end of the capillary tube 30 in the desired buffer vessel 60A, 60B or 60C and an external control signal on conductor 116 activates pressure control solenoid valve 88 putting a partial vacuum in the buffer reservoir by connecting it through tubes 94 and 114 to low-pressure vacuum tank 84. This pulls buffer from vessel 60A, 60B or 60C into the capillary tube 30, and into vessel 96, completely filling the capillary tube 30. Advantageously, the pressure sensor 104 should be programmable so that different degrees of reduced pressure or partial vacuum may be preset in the tank by the external controller or computer (not shown).

It is desirable that a higher vacuum be used to rapidly fill the tube and a lower vacuum be used to more slowly pick up a minute amount of sample. A typical higher vacuum is 500 centimeters of water or about one-half of an atmosphere. A typical lower vacuum is 12 inches of water. When it is desired to effect a separation, the vertical section of the capillary tube 30 dips into a sample tube such as 58A or 58B on sample holding reel 44. A minute amount of sample is withdrawn into the capillary tube 30 by the application of negative pressure on electrode buffer vessel 96.

When pressure control solenoid valve 88 operates to reduce the pressure in electrode buffer vessel 96, the pressure does not reduce instantaneously. This can cause an error in the sample volume. Since the bore of the capillary tube 30 is very small, under 100 micrometers, the flow induced by pressure differences of less than one atmosphere results in laminar flow; flow of a rate which is proportional to the pressure (transitional and turbulent flow result in flow rates that are not directly proportional to pressure). The volume of sample taken up is proportional to the time integral of the flow rate.

Since flow rate is proportional to pressure, the volume of the sample is therefore also proportional to the time integral of the negative gauge pressure within the electrode buffer vessel 96. Pressure sensor 104 monitors the negative gauge pressure within electrode buffer vessel 96 and transmits it through electrical lead 92 to electrical interface 82 and thence to an external controller or computer through lead 106. The external computer can either operate the pressure control solenoid valve 88 for a fixed time to reduce the pressure in vessel 96 while accumulating the integral of the reduced pressure and thereby tabulate sample volumes for display or for correction of peak data, or the controller can be programmed to iteratively determine the proper energization time of pressure control solenoid valve 88 to cause the sample to correspond to a predetermined amount.

After a sample is taken up into the end of the capillary tube 30 (only a very small amount of sample is taken up, often on the order of a nanoliter), movable arm 46 moves the end of the capillary tube 30 into one of the buffer vessels 60A, 60B or 60C. The high voltage power supply 14 is turned on, preferably also by automatic means, and the sample starts to migrate and separate in the capillary tube 30.

During the time that any sample components of interest are within the vertical section of capillary tube 30, attached to the movable arm 46, the voltage applied is low enough so that convection pattern in FIGS. 4 and 5 does not take place in spite of the vertical orientation in the capillary tube 30. Once the sample components of interest have migrated into the horizontal section of capillary tubing 30, which does not take very long since the vertical section is quite short, the voltage from the power supply 14 increases under the control of a program or manual control means to provide a rapid separation. Convection, if it forms due to the higher voltage which causes higher power dissipation within the capillary tube 30, is of the pattern shown in FIG. 6 which does not degrade resolution.

The separated sample zones migrate through the sensor 72 and are recorded by the absorbance monitor. When the separation is complete, sample holding reel 44 rotates one tube position, movable arm 46 moves the end of the capillary tubing 30 from the electrode buffer vessel 96 into the next sample tube, and the operation cycle repeats for the next sample. It should be noted that the buffer vessels must be filled with the same height and the electrode vessel buffer 96 must be vented to the atmosphere (pressure control solenoid valve 88 deenergized) during electrophoretic separation. If this precaution is not taken, buffer electrolyte will flow by siphon action through the capillary tube 30. This is undesirable since siphon flow within the capillar tube 30 has a laminar flow profile that induces axial mixing of the sample zones and degrades the resolution of the separation.

From the above description, it can be understood that the separating apparatus of this invention has several advantages, such as for example: (1) noise is reduced by the superior transmission of light from a light source through a very small sensing volume into the light detector; (2) band spreading is reduced by constraining convection currents in the medium to motion in a direction orthogonal to the direction of migration of the molecular species being sensed; and (3) greater precision of sample injection is provided.

Although a preferred embodiment of the invention has been described with some particularity, many modifications and variations are possible in the preferred embodiment in the light of the above teachings. Therefore, it is to be understood that, within the scope of the appended claims, the invention may be practiced other than as specifically described.

What is claimed is:

1. A method of performing electrophoresis comprising the steps of:

positioning a preselected length of capillary tube containing a separation medium in a support, with the capillary tube being coiled to fit a fixed area of the support wherein different lengths of capillary tubes may be placed in the same support;

mounting said support horizontally between a location for injection of samples and a location for the sensing of bands wherein the capillary tube is sufficiently horizontal between the location for injection of samples and the location for sensing bands to have no vertical lengths having a dimension greater than one third of the distance between the location for injecting samples and the location for sensing bands;

establishing a potential across the separating medium;

introducing a sample into the separating medium for electrophoresis through it;

using a potential sufficiently high to cause convection currents within said separating medium in a substantially horizontal portion of said separating medium under conditions in which there are no significant bands of sample being separated in a region with a substantially vertical component capable of causing band spreading by convection in the direction of migration.

2. A method according to claim 1 further including applying a potential sufficiently low to avoid convection currents within said supporting medium in said region with a substantially vertical component, wherein a potential lower than said potential sufficiently high to cause convection currents is used under some circumstances.

3. A method according to claim 1 in which said step of positioning includes the step of positioning a horizontal portion of the capillary tube that is at least 100 millimeters long in said support and a horizontal portion is at least 100 millimeters in length.

4. A method according to claim 1 further including the step of collecting at least one of said bands in a collection means.

5. A method according to claim 4 wherein said at least one of said bands is collected in a sample collection cup within said collection means in circuit with said capillary tube and a source of potential, wherein said source of potential also serves to cause electrophoresis in said capillary tube.

6. A method according to claim 4 in which said step of collecting includes the substep of collecting at least some different bands in correspondingly different containers.

7. A method according to claim 4 in which the step of collecting includes the step of collecting certain bands in a collection means containing a number of sample collection cups and moving the collection means by a carrier wherein different bands are collected in different collection cups.

8. A method according to claim 4 in which the step of collecting includes the-step of collecting at least one band in a salt trap.

9. A method according to claim 4 in which the step of collecting includes the step of collecting in one of a plurality of collecting cups having a membrane in contact with an electrolyte in a collection means holding the electrolyte and a plurality of collection cups and the step of applying a potential across said electrolyte and separating medium.

10. A method according to claim 1 further including the step of injecting a sample into said capillary tube by applying a pressure difference between said sample and at least a portion of said separating medium.

11. A method according to claim 10 in which the step of injecting a sample further includes the step of measuring a change in pressure as said sample is injected and using the measured change in pressure to indicate the amount of sample injected.

12. A method according to claim 11 in which the measured change in potential is integrated and a signal representing the integral of the measured change is used to indicate the amount of sample injected.

13. A method according to claim 1 further including the step of detecting said bands, said step of detecting said bands including the substeps of sensing bands in said capillary tube through said capillary tube over a controlled area having a length parallel to the longitudinal axis of said capillary tube and a width traverse to said longitudinal axis, wherein a maximum width is no greater than three times an inner diameter of said capillary tube and the minimum width being no less than one half the diameter of said inner diameter at said controlled area.

14. A method according to claim 13 further including the step of adjusting said controlled area for a maximum signal.

* * * * *